United States Patent [19]
Mythen

[11] Patent Number: 6,004,334
[45] Date of Patent: Dec. 21, 1999

[54] TONGUE CLEANING APPARATUS

[76] Inventor: Daniel Richard Mythen, 21307 NE. 97th Pl., Redmond, Wash. 98053

[21] Appl. No.: 09/083,333

[22] Filed: May 21, 1998

[51] Int. Cl.$^6$ .............................. A61B 17/24; A61F 9/00
[52] U.S. Cl. ............................................................ 606/161
[58] Field of Search .................................... 606/161, 162; 424/440, 474, 479; D1/127; D24/101

[56] References Cited

U.S. PATENT DOCUMENTS

| | | | |
|---|---|---|---|
| D. 88,675 | 12/1932 | Schoenleber | D8/DIG. 2 |
| D. 269,712 | 7/1983 | Tovey | D28/2 |
| D. 287,780 | 1/1987 | Farber | D1/106 |
| 4,847,090 | 7/1989 | Della Posta et al. | 424/440 |

*Primary Examiner*—Michael Buiz
*Assistant Examiner*—Vy Q. Bui
*Attorney, Agent, or Firm*—Dergosits & Noah LLP

[57] ABSTRACT

The present invention is a dissolvable candy which provides effective tongue scraping action. The candy is preferably lozenge-shaped with the top side generally opposing the bottom side. The top side is a soft pliable edible dissolvable candy material, such as a GUMMI-BEAR type confection, and the bottom side is a hard edible dissolvable candy material, such as hard peppermint. The top side preferably includes a depression formed in the center of it for allowing the top side to be removably adhered by suction to the roof of a user's mouth. The bottom side has a cleaning pattern formed in it which is suitable for abrading the user's tongue in the mouth. Preferably, the pattern is a symmetrical raised pattern, such as a raised star pattern.

9 Claims, 1 Drawing Sheet

TONGUE CLEANING APPARATUS

FIELD OF THE INVENTION

The present invention relates to a tongue cleaning apparatus, and more specifically, to a lozenge-shaped candy which has one side which is soft and pliable for removably adhering to the roof of the user's mouth, while the opposing side is hard with a cleaning pattern defined thereon for gently abrading the tongue to remove malodorous films.

BACKGROUND OF THE INVENTION

Oral malodor, also known as bad breath or halitosis, is a common condition afflicting many people. The origin of oral malodor may be physiological or pathological in nature. However, even for individuals having healthy periodontal tissues and practicing good oral hygiene, the back of the tongue is a significant source of oral malodor due to the production of volatile sulfur compounds.

Various devices are known for addressing oral malodor. For example, U.S. Pat. No. 5,226,197 discloses a tongue hygiene device shaped like a toothbrush but with a wider than normal head, short bristles and a scraper. Sky Mall Magazine markets a tongue scraper which is made from surgical stainless steel and has two handles which allow the user to insert the scraper into the mouth and pull it across the tongue. However, it remains desirable to have an easy-to-use device that helps fight oral malodor, and the present invention is directed to such a device.

SUMMARY OF THE INVENTION

The present invention is a candy suitable for dissolving in the mouth while providing effective tongue scraping action by virtue of a cleaning pattern formed in the candy. In the preferred embodiment, the candy is lozenge-shaped with a top side generally opposing a bottom side. The two sides are adhered by an edible adhesive. The top side is a pliable edible dissolvable material, such as that used in GUMMI-BEAR type confections. Preferably, a depression is formed in the center of the top side for allowing it to be removably adhered by suction to the roof of a user's mouth.

The bottom side is a hard edible dissolvable material, such as hard peppermint candy. The bottom side has a cleaning pattern formed in it which is suitable for abrading a tongue in the mouth. Preferably, the pattern is a symmetrical raised pattern, such as a raised star pattern.

In use, the candy is adhered by its top side to the roof of the mouth and the user's tongue passes over the cleaning pattern formed in the bottom side. The candy may be repeatedly removed and adhered in a new spot to permit more thorough coverage of the tongue until the candy is dissolved.

A better understanding of the features and advantages of the present invention will be obtained by reference to the following detailed description of the invention and accompanying drawings which set forth an illustrative embodiment in which the principles of the invention are utilized.

DETAILED DESCRIPTION OF THE INVENTION

Figure 1:
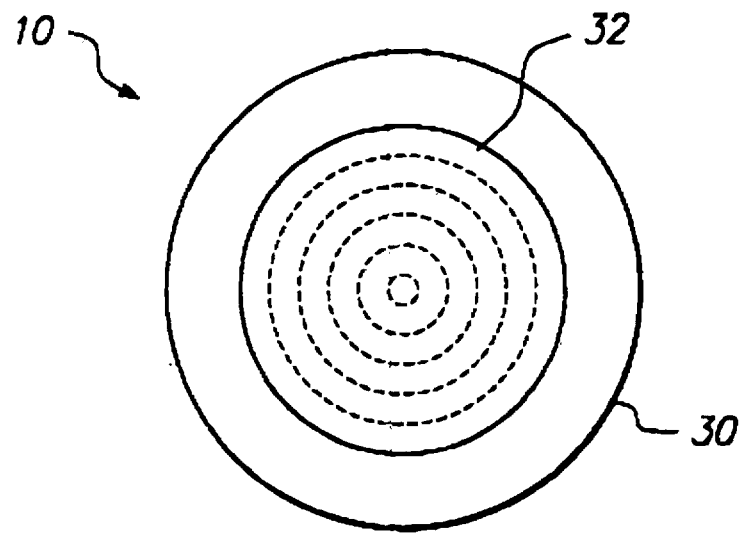
FIG. 1 is a top plan view of the preferred embodiment of a tongue cleaning apparatus in accord with the present invention.
Figure 2:
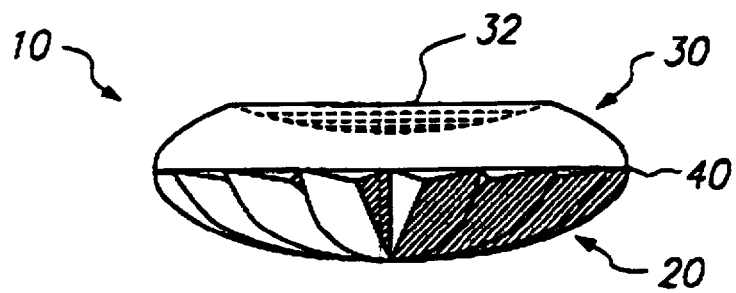
FIG. 2 is a side elevation view of the tongue cleaning apparatus of FIG. 1.
Figure 3:
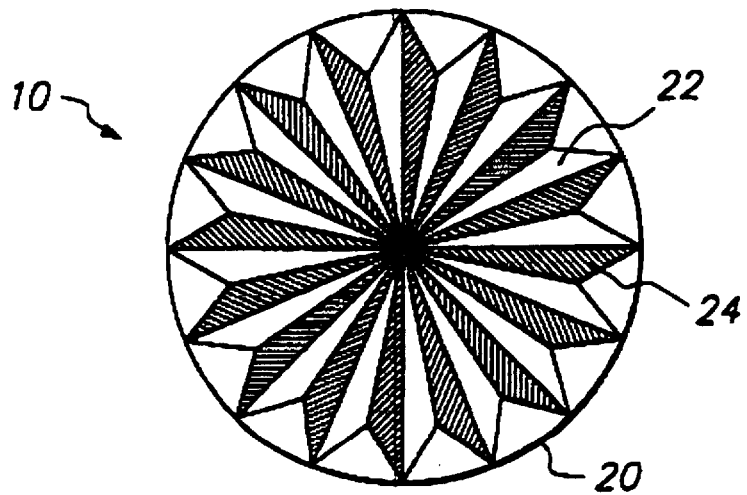
FIG. 3 is a bottom plan view of the tongue cleaning apparatus of FIG. 1.

Referring to FIGS. 1–3, the present invention includes a generally lozenge-shaped candy 10 having a hard side 20 and a soft side 30. In the preferred embodiment, the diameter of the candy 10 is approximately ⅞ inch to 1 inch and the thickness of the candy is approximately ⅜ inch.

The soft side 30 is preferably a soft, pliable, dissolvable gelatinous candy material, such as that used in GUMMI-BEAR or GUMMI-WORM type confections. A circular depression 32 is formed in the center of the soft side 30 to permit the soft side to be adhered to the roof of the mouth by suction. For example, the depression may be approximately ½ inch in diameter by ⅛ inch deep. The candy 10 may thus be easily removed from one spot on the roof of the mouth and moved to another.

The hard side 20 is preferably a hard dissolvable candy material, such as any commercially available hard peppermint candy. The hard candy material is formed by conventional confectionery methods to have a pattern 22, such as by molding or stamping. For example, the illustrated pattern 22 is a sixteen-point star defined by ridges 24 which extend from the surface of the hard candy approximately 1/16 inch high. The ridges 24 provide a rigid scraping surface that abrades the tongue as it passes over the candy. Other patterns may prove equally effective. The use of raised ridges or fins extending from the surface of the hard candy is preferred, but it is conceivable that a sufficiently abrasive pattern could be formed in the surface, for example, by etching concentric circles or some other pattern in the hard candy.

The hard side 20 and soft side 30 are bonded together with a thin layer 40 of confectioners adhesive or suitable equivalent in a well known manner. Also, a freshening agent, such as retsyn or other suitable equivalents, may be included with the candy, for example, on the hard side 20.

In use, the candy 10 may be repeatedly removed and reapplied via its soft side 30 to different positions in the mouth. By moving the position of the candy in the mouth, a more thorough coverage of the tongue by the abrasive scraping action of the candy is provided. Such action may be repeated until the candy is fully dissolved.

It should be understood that the invention is not intended to be limited by the specifics of the above-described embodiment, but rather defined by the accompanying claims. For example, dimensions and materials are specified for the preferred embodiment, but many variations will be obvious to one with skill in such matters.

I claim:

1. A tongue cleaning apparatus, comprising a lozenge-shaped edible dissolvable candy having one side formed with a cleaning pattern suitable to provide abrasive friction to a tongue when the candy is held in a mouth and an other side formed with a depression formed therein to facilitate adhering the other side to a roof of the mouth, wherein the one side comprises a hard dissolvable candy material and the other side comprises a soft pliable dissolvable candy material.

2. A tongue cleaning apparatus as in claim 1, wherein the pattern includes raised portions which extend above a surface of the one side.

3. A tongue cleaning apparatus as in claim 2, wherein the pattern is a star pattern.

4. A lozenge-shaped candy as in claim 1, wherein the one side is adhered to the other side by an edible adhesive.

5. A lozenge-shaped candy, comprising a hard side having an abrasive cleaning pattern formed thereon and a soft side having a depression formed therein to permit adhering the candy to a roof of a mouth with suction.

6. A lozenge-shaped candy as in claim 5, wherein the pattern includes raised portions which extend above a surface of the hard side.

7. A lozenges-shaped candy as in claim 6, wherein the pattern is a star pattern.

8. A lozenge-shaped candy as in claim 5, wherein the hard side is adhered to the soft side by an edible adhesive.

9. A tongue cleaning apparatus, comprising a top side and a bottom side opposing the top side, wherein the top side is adhered to the bottom side by an edible adhesive, and wherein the top side is a pliable edible dissolvable candy material having a depression formed therein for allowing the top side to be adhered by suction to a roof of a mouth, and wherein the bottom side is a hard edible dissolvable candy material having a cleaning pattern formed therein for abrading a tongue in the mouth.

\* \* \* \* \*